(12) United States Patent
Kajiyama et al.

(10) Patent No.: US 10,473,614 B2
(45) Date of Patent: Nov. 12, 2019

(54) GAS SENSOR

(71) Applicant: DENSO CORPORATION, Kariya, Aichi-pref. (JP)

(72) Inventors: Norikazu Kajiyama, Kariya (JP); Makoto Ito, Kariya (JP); Yasufumi Suzuki, Kariya (JP)

(73) Assignee: DENSO CORPORATION, Kariya (JP)

( * ) Notice: Subject to any disclaimer, the term of this patent is extended or adjusted under 35 U.S.C. 154(b) by 170 days.

(21) Appl. No.: 15/322,781

(22) PCT Filed: Jun. 30, 2015

(86) PCT No.: PCT/JP2015/068866
§ 371 (c)(1),
(2) Date: Dec. 29, 2016

(87) PCT Pub. No.: WO2016/002793
PCT Pub. Date: Jan. 7, 2016

(65) Prior Publication Data
US 2017/0108463 A1    Apr. 20, 2017

(30) Foreign Application Priority Data

Jun. 30, 2014   (JP) ................................ 2014-133486
Feb. 12, 2015   (JP) ................................ 2015-025182

(51) Int. Cl.
*G01N 27/407* (2006.01)
*G01N 27/41* (2006.01)
*G01N 27/406* (2006.01)

(52) U.S. Cl.
CPC ..... *G01N 27/4077* (2013.01); *G01N 27/4067* (2013.01); *G01N 27/41* (2013.01)

(58) Field of Classification Search
CPC .................. G01N 27/407; G01N 27/4067
See application file for complete search history.

(56) References Cited

U.S. PATENT DOCUMENTS

| 6,354,134 B1 | 3/2002 | Katafuchi et al. |
| 6,432,289 B1 | 8/2002 | Uchida et al. |
| 2006/0024202 A1* | 2/2006 | Atsumi ............. G01N 27/4075 422/78 |
| 2012/0018304 A1* | 1/2012 | Mikami ............. G01N 27/4076 204/427 |

* cited by examiner

*Primary Examiner* — Alexander S Noguerola
(74) *Attorney, Agent, or Firm* — Nixon & Vanderhye P.C.

(57) ABSTRACT

A gas sensor is provided which has a rapid heating property and which can detect A/F ratio with high accuracy and can detect specifically a stoichiometric environment with high accuracy. The gas sensor has a limiting current type gas sensor element. The gas sensor element has a cup-shaped solid electrolyte, a reference electrode formed on an inside surface of the solid electrolyte, a measuring electrode formed on an outside surface of the solid electrolyte and a heater. The heater is disposed inside the solid electrolyte so that a tip end thereof contacts the inside surface of the solid electrolyte. The gas sensor outputs the limiting current value depending on an oxygen concentration in exhaust gases by applying a predetermined voltage between the reference electrode and the measuring electrode. The measuring electrode, which a length thereof in a direction is 0.5 mm to 3.0 mm, is housed in a range 0.5 mm to 7.5 mm from a tip end of the solid electrolyte in the direction.

13 Claims, 7 Drawing Sheets

GAS SENSOR

This application is the U.S. national phase of International Application No. PCT/JP2015/068866 filed Jun. 30, 2015 which designated the U.S. and claims the benefit of priority from earlier Japanese Patent Applications No. 2014-133486 filed on Jun. 30, 2014, and No. 2015-25182 filed on Feb. 12, 2015, the entire contents of each of which are hereby incorporated by reference.

TECHNICAL FIELD

This invention relates to a gas sensor.

BACKGROUND ART

A conventionally used gas sensor detects an oxygen concentration included in the exhaust gases which are exhausted from an internal combustion engine or the like for air-fuel ratio control. For example, a gas sensor where a gas sensor element, which includes a so-called cup-shaped solid electrolyte, a reference electrode 220, a measuring electrode and a heater, is incorporated (refer to Patent Document 1, for example). The reference electrode 220 is disposed on an internal surface of the solid electrolyte. The measuring electrode is disposed on a lateral surface on the gas sensor. The heater is disposed on an inside surface of the solid electrolyte. The gas sensor is used in a state that the solid electrolyte is heated and activated by the heater.

RELATED ART

Patent Document

[Patent Document 1] Japanese Unexamined Patent Application No. 8-271474

DISCLOSURE OF THE INVENTION

Problems to be Solved by the Invention

Recently, in an internal combustion engine, reduction of an amount of catalytic precious metals and reliability of purification efficiency of exhaust gases are further demanded. Specifically, it is demanded that an air-fuel ratio of the internal combustion engine is controlled stoichiometrically in a state which has a high purifying capacity by catalyst. In addition, it is required to detect A/F with high accuracy even in a state just after starting the internal combustion engine or under a small amount of a gas atmosphere (ppm order) in the stoichiometric environment to increase the purification efficiency of the exhaust gases. However, it is required that a gas sensor is used in a state that a solid electrolyte of a gas sensor element is activated by heat as described above. Thereby, it is difficult to detect A/F just after starting the internal combustion engine with high accuracy when the gas sensor element is not sufficiently heated just after starting the internal combustion engine. Further, when there is a temperature variation in a detection part of the gas sensor element (i.e. measuring electrodes and a reference electrode), the A/F ratio may be not detected with high accuracy and also unevenness may occur in a detection performance of the detection part of the gas sensor element. Specifically, a stoichiometric air-fuel ratio may be not detected due to a variation of a gaseous adsorption reactivity if the amount of the gas is small in the stoichiometric environment. Therefore, conventionally, thermal uniformity of the detection part is secured by heating the gas sensor element using radiated heat of a heater and the variation of the detection performance (gaseous adsorption reactivity) is controlled. However, a long time is required until the temperature of the gas sensor element is heated to the activation temperature since radiated heat is used and rapid heating capability becomes inferior. Thereby, from such a viewpoint, it is difficult to detect A/F just after starting the internal combustion engine with high accuracy and the stoichiometric air-fuel ratio with high accuracy.

The present invention provides a gas sensor which has excellent rapid heating capability, capable of detecting A/F with high accuracy, and capable of specifically detecting the stoichiometric air-fuel ratio with high accuracy.

Means for Solving the Problems

One aspect of a gas sensor of the present invention provides a solid electrolyte, reference electrode, measuring electrode and a heater. The solid electrolyte has a cup-shaped closed-end cylindrical shape. The reference electrode is formed on an inside surface of the solid electrolyte. The measuring electrode is formed on an outside surface of the solid electrolyte. The heater has a heating part heating the solid electrolyte. The heater is disposed inside the solid electrolyte in a state that a tip of the heater contacts the inside surface of the solid electrolyte. The gas sensor of the present invention includes a limiting current type gas sensor element. The limiting current type gas sensor is configured to output a limiting current value depending on a specific gas concentration in measured gases by applying a predetermined voltage between the reference electrode and the measuring electrode. In the gas sensor, an axial length of the measuring electrode is 0.5 mm to 3.0 mm. Further, the measuring electrode is provided so as to fall within a range of 0.5 mm to 7.5 mm from a tip of the solid electrolyte in an axial direction of the solid electrolyte.

Effects of the Invention

In the gas sensor, thermal conduction from the heater to the solid electrolyte is prompted and rapid heating capability of the solid electrolyte is improved since the heater contacts the inside surface of the solid electrolyte. Further, the length of the axial direction of the measuring electrode is 0.5 mm to 3.0 mm. Further, the measuring electrode is provided so as to fall within the range of 0.5 mm to 7.5 mm from the tip of the solid electrolyte in the axial direction of the solid electrolyte. That is to say, the measuring electrode is formed so as to have a sufficiently short length in the axial direction. In addition, the measuring electrode is provided so as to fall within a predetermined range from the tip of the solid electrolyte. Thereby, the temperature variation and the variation of the detection performance in the measuring electrode may be controlled. Specifically, with a small amount of the gas in the stoichiometric environment, the variation of the gaseous adsorption reactivity is reduced and a variation of stoichiometric detection performance is controlled. From these results, A/F just after starting the internal combustion engine and A/F with only a small amount of the gas in the stoichiometric environment (ppm order) may be detected with high accuracy. In addition, mounting the gas sensor on a downstream catalyst of vehicles (rear mounting) with a small amount of the gas in the stoichiometric environment allows to always detect A/F with high accuracy and to be applicable to stoichiometric control.

The present invention provides the gas sensor which has excellent rapid heating capability, capable of detecting A/F with high accuracy, and capable of specifically detecting the stoichiometric air-fuel ratio with high accuracy as described above.

MODE FOR CARRYING OUT THE INVENTION

A gas sensor of the present invention may be used for a detection apparatus of specific gas concentration in exhaust gases or the like of an internal combustion engine which is mounted on automobiles or the like.

EMBODIMENTS

First Embodiment

A gas sensor of the present invention is described below using FIG. 1 to FIG. 9.

Figure 1:
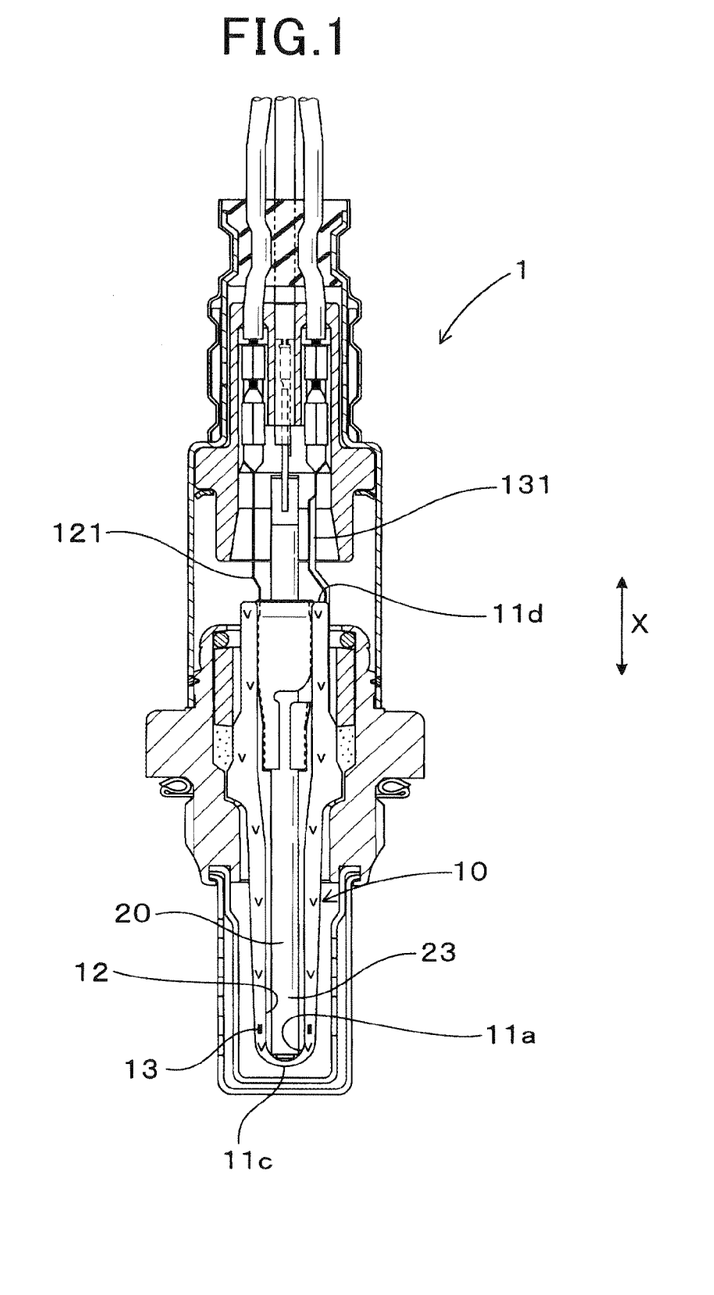
FIG. 1 shows a cross-sectional view of a gas sensor where is provided a gas sensor element according to a first embodiment of the present invention.

A gas sensor 1 of the present embodiment has a gas sensor element 10. The gas sensor element 10 has, as can be seen in FIG. 1, a solid electrolyte 11, a reference electrode 12, a measuring electrode 13 and a heater 20. The solid electrolyte has a cup-shaped closed-end cylindrical shape. The reference electrode 12 is formed on an inside surface 11a of the solid electrolyte 11. The measuring electrode 13 is formed on an outside surface 11b of the solid electrolyte 11. The heater 20 has a heating part 23 heating the solid electrolyte 11. And the heater 20 is disposed inside the solid electrolyte 11 in a state that a tip end 22a of the heater 20 contacts the inside surface 11a of the solid electrolyte 11.

Figure 2:
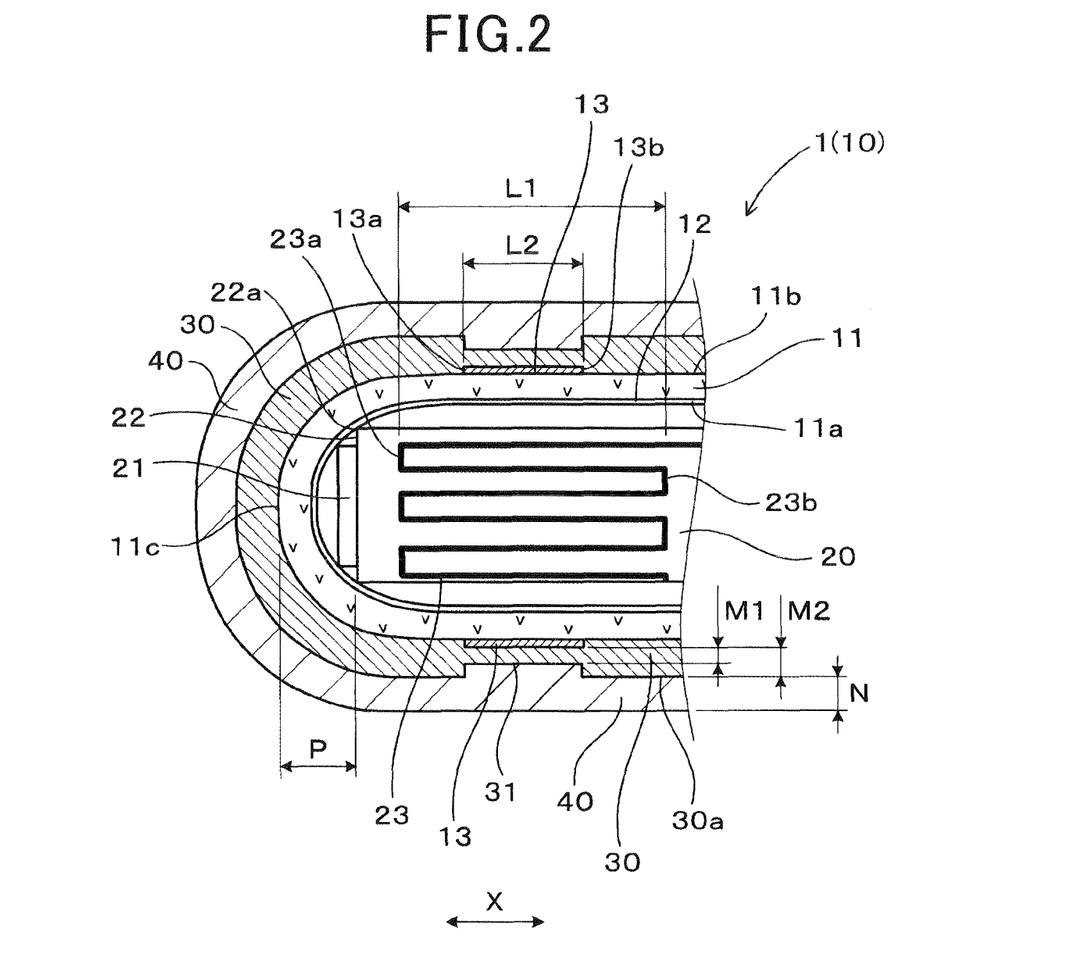
FIG. 2 shows a sectional partial enlarged view of the gas sensor element according to the first embodiment.

In addition, the gas sensor element 10 is a limiting current type gas sensor element. The limiting current type gas sensor is configured to output a limiting current value depending on the specific gas concentration in measured gases by applying predetermined voltage between the reference electrode 12 and the measuring electrode 13. As shown in FIG. 2, a length L2 of the measuring electrode 13 in an axial direction X is 0.5 mm to 3.0 mm. Further, the measuring electrode 13 is provided so as to fall within a range of 0.5 mm to 7.5 mm from a tip end 11c (a tip of the outside surface 11b) of the solid electrolyte 11 in an axial direction X of the solid electrolyte 11.

As shown in FIG. 1, in the example, "tip end side" is one end side, exposed to the measured gases, of the gas sensor 1 of an axial direction X of the gas sensor 1. In addition, the "base end side" is opposed to the tip end side in the axial direction of the gas sensor 1.

The gas sensor 1 of the example is described below.

The solid electrolyte 11 is made up of zirconia-based ceramic. The solid electrolyte 11 has a cup-shaped closed-end cylindrical shape. The axial direction (longitudinal direction) of the solid electrolyte 11 is defined as X. In the axial direction X, an opening side end part of the solid electrolyte 11 (i.e. upper end portion of a paper of FIG. 1) is defined as a base end 11d. Further, one end on an opposite side of the base end 11d in the axial direction X is defined as the tip end 11c. As shown in FIG. 2, the tip end 11c is hemispherically curved.

The heater 20 is disposed inside the solid electrolyte 11. The heater 20 has an axle 21 of the bar-shaped ceramic and a sheet-like heating member 22 which is wound around the axle 21. The tip corner part 22a of the heating member 22 contacts the inside surface 11a (the reference electrode 12) which is curved in the tip end 11c of the solid electrolyte 11. The tip corner part 22a is provided so as to fall within a range of 1.5 mm to 2.0 mm from the tip end 11c in the axial direction X.

The heating member 22 has, as shown in FIG. 2, the heating part 23 which is disposed on side of the tip end 11c and which is heated by energization of the heating member 22. A length L1 of the heating part 23 in the axial direction X may be set to be 3.0 mm to 7.0 mm. In the axial direction X, the heating part 23 is provided so as to fall within a range of 0.25 mm to 9.0 mm from the tip end 22a of the heater 20. Thereby, as shown in FIG. 2, the heating part 23 is disposed near the tip end 22a of the heater 20. In addition, at least part of the heating part 23 (all of the heating part 23 in the example) is opposed to the measuring electrode 13.

The reference electrode 12 is formed inside an inner periphery 11a of the solid electrolyte 11 and is formed on a part of a part which is opposed to the heating part 23 of the heater 20. The reference electrode 12 is formed over the entire circumference in a circumferential direction of the inner periphery 11a of the solid electrolyte 11. The measuring electrode 13 is formed on an approximately whole area of an outside surface 11b of the solid electrolyte 11. As shown in FIG. 1, the reference electrode 12 and the measuring electrode 13 are respectively connected with lead wires 121 and 131 which are pulled out from side of the base end 11d.

As shown in FIG. 2, the axial length L2 of the measuring electrode 13 is 0.5 mm to 3.0 mm. When the length L2 is less than 0.5 mm, there is a risk that sensor output becomes small and detection accuracy is not sufficiently obtained. When the length L2 is over 3.0 mm, there is a risk that detection accuracy is reduced due to a variation of temperature in the measuring electrode 13.

As shown in FIG. 2, the measuring electrode 13 is provided so as to fall within the range of 0.5 mm to 7.5 mm from the tip end 11c of the solid electrolyte 11. In addition, in the example, in the outside surface 11b of the solid electrolyte 11, the measuring electrode 13 is provided so as to fall a range (a range shown by an arrow L1 in FIG. 2) which is opposed to the heating part 23.

As shown in FIG. 2, a diffusion resistance layer 30 is disposed outside the solid electrolyte 11. The diffusion resistance layer 30 is made up of a porous body and at least covers the measuring electrode 13. In the example, the diffusion resistance layer 30 covers an entire outside surface of the solid electrolyte 11. The diffusion resistance layer 30 is formed by applying ceramic coating to the outside of the solid electrolyte 11. A thickness M1 on the measuring electrode 13 of the diffusion resistance layer 30 may be 400 µm to 700 µm, preferably 450 µm to 600 µm.

A porosity of the diffusion resistance layer 30 may be 2.0% to 8.0%, preferably 4.5% to 5.5%. Incidentally, in the example, the porosity of the diffusion resistance layer 30 may be determined by an Archimedes method.

As shown in FIG. 2, the diffusion resistance layer 30 is formed so as to be across an outside surface 13b of the measuring electrode 13 and the outside surface 11b of the solid electrolyte 11. In addition, the thickness M1 on the measuring electrode 13 of the diffusion resistance layer 30 and a thickness M2 are satisfied a relationship M2/M1≤1.35, preferably M2/M1≤1.25. The thickness M2 is a thickness of the diffusion resistance layer 30 on the outside surface 11b of the solid electrolyte 11 other than the measuring electrode 13. As shown in FIG. 2, in the specification, "the thickness M1 on the measuring electrode 13 of the diffusion resistance layer 30" is defined as a distance from the outside surface of the measuring electrode 13 to an outside surface 30a of the diffusion resistance layer 30. In addition, "the thickness M2 of the diffusion resistance layer 30 on the outside surface 11b of the solid electrolyte 11 other than the measuring electrode 13" is defined as a distance from a position equivalent to the outside surface of the measuring electrode 13 to the outside surface 30a of the diffusion resistance layer 30. The position equivalent to the outside surface of the measuring electrode 13 is in an area where the measuring electrode 13 is not formed on the outside surface 11b of the solid electrolyte 11. In the example, M1 and the M2 are satisfied a relationship M1<M2, a convex part 31 is formed on a part which is opposed to the measuring electrode 13 in the outside surface 30b of the diffusion resistance layer 30.

As shown in FIG. 2, a porous protection layer 40 having a higher porosity than the diffusion resistance layer 30 is formed on the outside surface 30b of the diffusion resistance layer 30. The protection layer 40 is mounted for trapping poisoning components in the measured gases (exhaust gases). The protection layer 40, which carries platinum, is made up of ceramic made of alumina. In the example, the protection layer 40 is mounted so as to cover the entire outside surface 30b of the diffusion resistance layer 30. A thickness N of the protection layer 40 may be set to a desired thickness. The porosity of the protection layer 40 may be set to be 50% to 90%. Incidentally, in the example, the porosity of the protection layer 40 may be determined by the Archimedes method.

(Evaluation Temperature Variation)

Relations between a contact location (the tip corner part 22a) between the heater 20 and the solid electrolyte 11 and the temperature variation of the outside surface 11b of the solid electrolyte 11 were examined. Specifically, the length L1 of the heating part 23 of the heater 20 was set to be 3 mm, and a determined temperature was set to be 700° C. In addition, while changing a distance P by 0.5 mm width within a range of 1.0 mm to 2.5 mm, each of the temperature of the outside surface 11b corresponding to the respective cases was determined so as to fall within a range of 8.0 mm from the tip end 11c. The distance is a distance between the contact location (the tip corner part 22a) of the heater 20 and the tip end 11c. A reference temperature $T_0$ was set to be 600° C., at which the difference is reduced by the gas species adsorption/desorption reaction with respect to the electrode. The variation of the temperature (element temperature) of the outside surface 11b for a determined temperature was determined.

Figure 3:
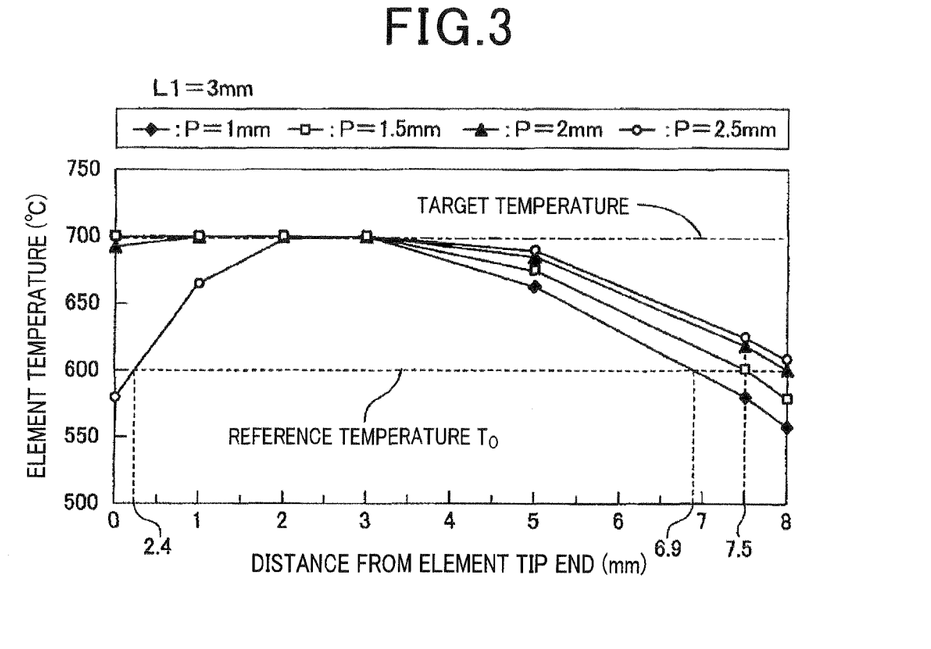
FIG. 3 is a pattern graph showing relations between a forming position of a heating part and an element temperature according to the first embodiment.

As shown in FIG. 3, when P is 1.0 mm, the element temperature was not less than the reference temperature $T_0$ (600° C.) in a range that a distance from the tip end 11c is less than 6.9 mm. On the other hand, the element temperature was lower than the reference temperature $T_0$ in a range that the distance from the tip end 11c of the solid electrolyte 11 is 6.9 mm to 8.0 mm.

When P is 1.5 mm, the element temperature was not less than the reference temperature $T_0$ in a range such that the distance from the tip end 11c of the solid electrolyte 11 is not more than 7.5 mm. In addition, the element temperature was lower than the reference temperature $T_0$ in a range such that the distance from the tip end 11c of the solid electrolyte 11 is more than 7.5 mm and not more than 8.0 mm.

When P is 2.0 mm, the element temperature was higher than the reference temperature $T_0$ in a range such that the distance from the tip end 11c of the solid electrolyte 11 which is the entire measuring range is not more than 8.0 mm.

When P is 2.5 mm, the element temperature was higher than the reference temperature $T_0$ in a range such that the distance from the tip end 11c of the solid electrolyte 11 is less than 0.24 mm. In addition, the element temperature was higher than the reference temperature $T_0$ in a range such that the distance from the tip end 11c of the solid electrolyte 11 is 0.24 mm to 8.0 mm.

That is to say, in such conditions, it was shown that the variation of the temperature when P is 1.5 mm to 2.0 mm was small in a range such that the distance from the tip end 11c is not more than 7.5 mm.

Next, the relationship between the length L1 of the heating part 23 of the heater 20 and the variation of the temperature of the outside surface 11b of the solid electrolyte 11 was examined. Specifically, as shown in FIG. 2, the distance P between the contact location (the tip corner part 22a) of the heater 20 and the tip end 11c was set to be 1.5 mm. While changing the length L1 of the heating part 23 in the axial direction X, each of the temperature of the outside surface 11b corresponding to the respective cases was determined.

Figure 4:
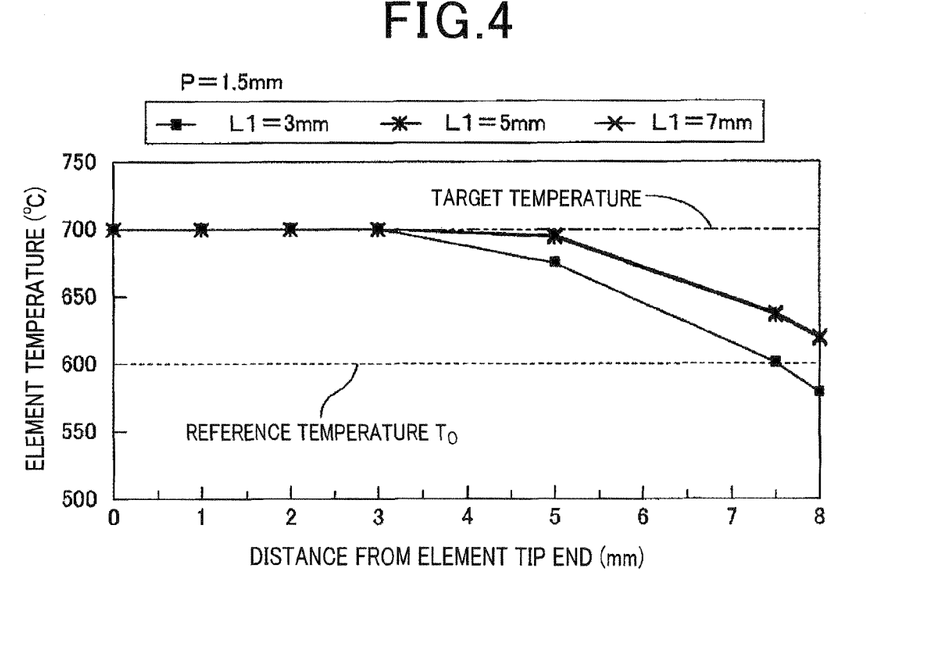
FIG. 4 is a pattern graph showing relations between a length of the heating part and the element temperature according to the first embodiment.

As shown in FIG. 4, in a range that the distance from the tip end 11c is not more than 7.5 mm, both the tip end part and the base end part were higher than the reference temperature $T_0$ at any L1. Further, when L1 is 5.0 mm and/or 7.0 mm, the variation of the temperature does not existed between the two. That is to say, in such conditions, it was shown that the variation of the temperature when L1 is not less than 3.0 mm was small. In addition, in a range where the distance from the tip end 11c is not more than 7.5 mm, the variation of the temperature when Li is not less than 7.0 mm was small. However, lengthening excessively the heating part 23 allows consumed power of the heater 20 to increase wastefully. Thereby L1 is preferably 3.0 mm to 7.0 mm.

(Sensor Output Evaluation)

Figure 5:
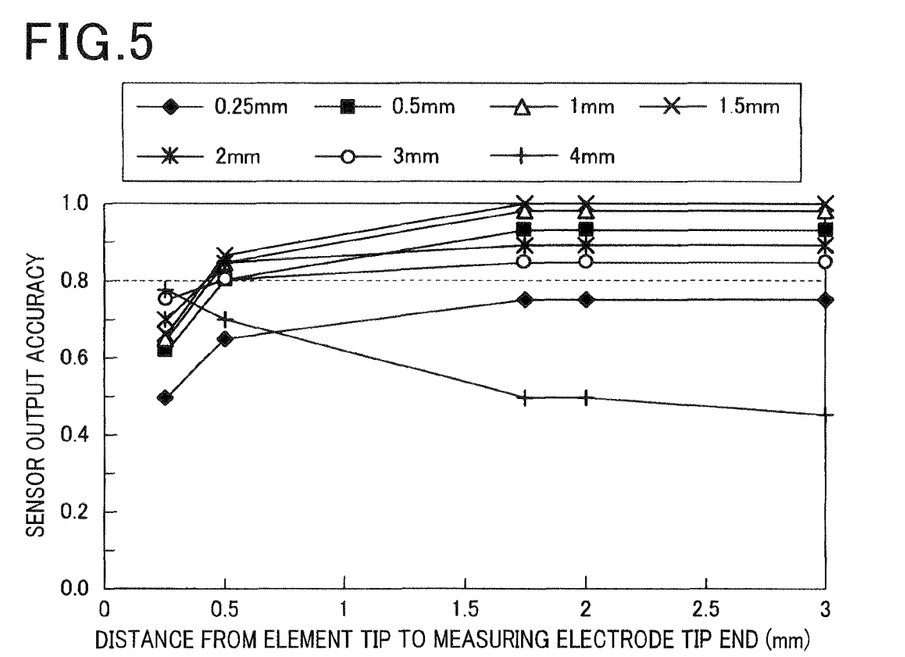
FIG. 5 is a pattern graph showing relations between the forming position of the heating part and a sensor output according to the first embodiment.
Figure 6:
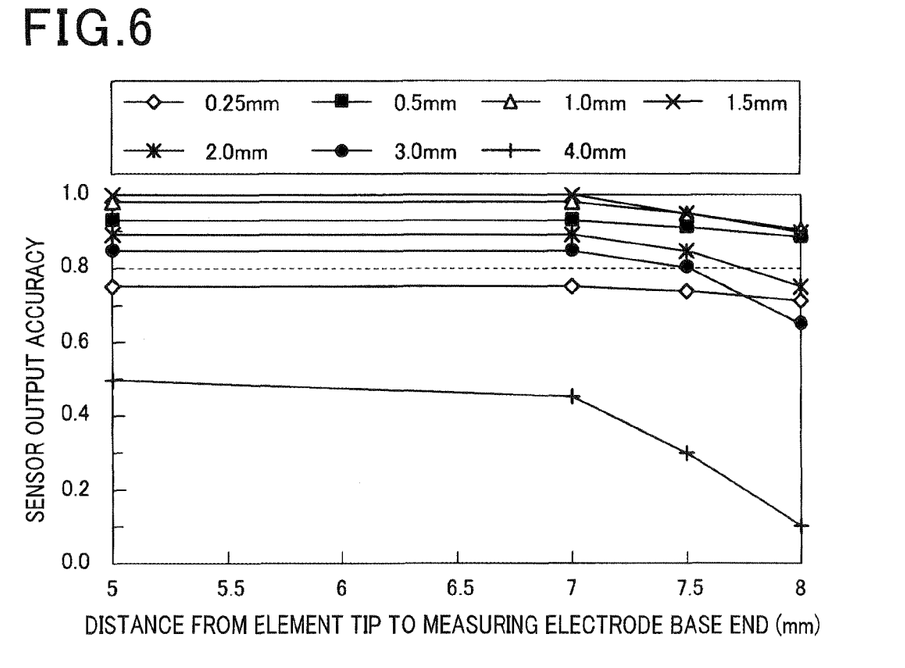
FIG. 6 is a pattern graph showing relations between the forming position of the heating part and the sensor output according to the first embodiment.

Relationships between the sensor output and a length L2 of the measuring electrode 13 and a forming position of the measuring electrode 13 were examined. Specifically, as shown in FIG. 5, first, a length L2 of the measuring electrode 13 which was respectively 0.25 mm, 0.5 mm, 1.0 mm, 1.5 mm, 2.0 mm, 3.0 mm and 4.0 mm was used. A sensor output value $IL_1$ was determined about each of a tip end part 13a (a tip end of the measuring electrode) and each of a base end part 13b (a base end of the measuring electrode) of the respective measuring electrode 13 while changing the distance from the tip end 11c. In addition, a determined output value of the gas sensor element 10 was defined as $IL_0$. A stored displacement ratio ($IL_1/IL_0$) of the each of $IL_1$ to $IL_0$ was calculated as a sensor output accuracy. It is necessary that the sensor output accuracy is not less than 0.8 to obtain a sufficient A/F detection accuracy. As shown in FIG. 5 and FIG. 6, it was shown that the sensor detection accuracy is not less than 0.8 when the length L2 of the measuring electrode 13 is 0.5 mm to 3.0 mm and when the forming position of the measuring electrode 13 is in a range that the distance from the tip end 11c is 0.5 mm to 7.5 mm. Further, it was shown that the sensor output accuracy is substantially not changed and is stable when the forming position of the measuring electrode 13 is in a range such that the distance from the tip end 11c is 1.75 mm to 7.0 mm. In addition, when a temperature of the measuring electrode 13 is less than 600° C., the difference becomes large by the gas species adsorption/desorption reaction with respect to the measuring electrode 13, and the detection accuracy is reduced. Thereby, the temperature of the measuring electrode 13 is preferably not less than 600° C. to further enhance the detection accuracy.

(Evaluation of a Thickness of the Diffusion Resistance Layer)

Figure 7:
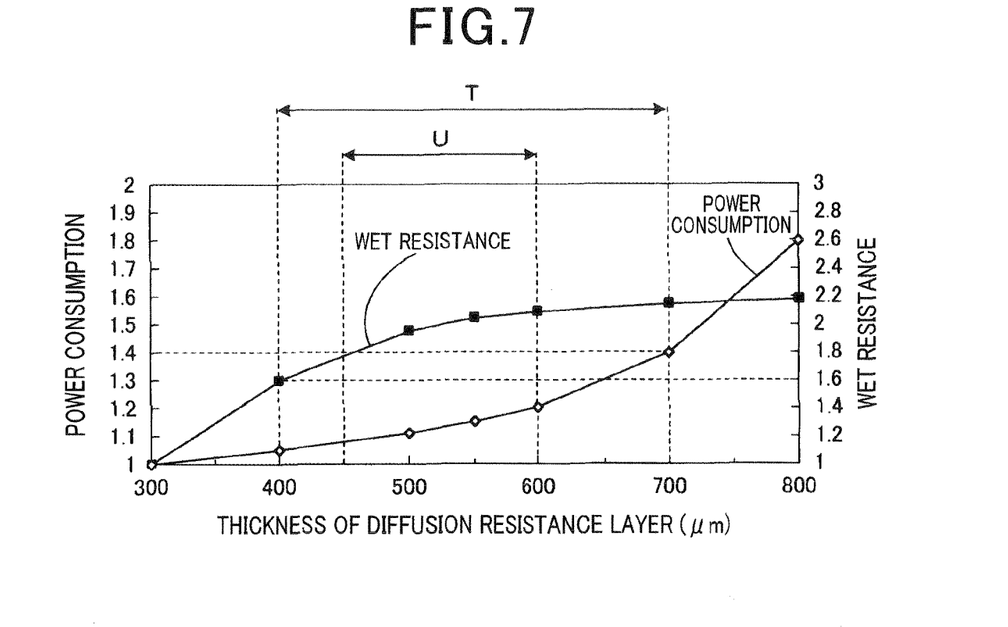
FIG. 7 is a pattern graph showing relations between a thickness of a diffusion resistance layer and a consumed power according to the first embodiment.

In the gas sensor 1, the consumed power when the thickness M1 is changed in a range of 300 μm to 800 μm was compared with the consumed power when the thickness the M1 is 300 μm. The thickness M1 is a thickness on the measuring electrode 13 of the diffusion resistance layer 30. Specifically, the consumed power when M1 is 300 μm is defined as 1. A consumed power ratio in the gas sensor 1 of the example was calculated about the consumed power in a driving mode LA#4. When the consumed power ratio is above 1.4, it was concerned about an influence on a fuel consumption. Thereby, it is necessary that the consumed power ratio is not more than 1.4. In addition, to suppress the consumed power from increasing, it is necessary that the consumed power ratio is not more than 1.2. As shown in FIG. 7, when the thickness M1 on the measuring electrode 13 of the diffusion resistance layer 30 is not more than 700 μm, it was shown that the consumed power is not more than 1.4. In addition, when the thickness M1 on the measuring electrode 13 of the diffusion resistance layer 30 is not more than 600 μm, it was shown that the consumed power is not more than 1.2.

Additionally, in the gas sensor 1, a wet resistance when the thickness M1 is changed in a range of 300 μm to 800 μm was compared with the wet resistance when the thickness M1 is 300 μm. The thickness M1 is the thickness on the measuring electrode 13 of the diffusion resistance layer 30. Specifically, the element temperature of a part 3 mm away from an element tip was set to be 700° C. In addition, water droplets were dropped at a position 3 mm from the tip end 11c toward the base end 11d. This was performed to gradually increase an amount of the dropped water droplet until a crack is generated in the gas sensor element 10. The amount of the dropped water droplet when the crack is generated was caused by water resistance. The water resistance when M1 is 300 μm was set to be 1. The water resistance was calculated while changing M1 within a range of 300 μm to 800 μm. It is necessary that the water resistance is not less than 1.6 to withstand use in a rear environment. Furthermore, it is necessary that the water resistance is not less than 1.8 to obtain sufficient reliability in use in the rear environment. As shown in FIG. 7, when the thickness M1 of the diffusion resistance layer 30 is not less than 400 μm, it was shown that the water resistance is not less than 1.6. Further, when the thickness M1 of the diffusion resistance layer 30 is not less than 450 μm, it was shown that the water resistance is not less than 1.8.

From the above-described evaluation of consumed power and the water resistance, it was confirmed that the thickness M1 on the measuring electrode 13 of the diffusion resistance layer 30 requires a range indicated by an arrow T in FIG. 7. The range indicated by the arrow T in FIG. 7 is, specifically, 400 μm to 700 μm. Further, it was shown that the thickness M1 on the measuring electrode 13 of the diffusion resistance layer 30 is preferably in a range indicated by an arrow U in FIG. 7. The range indicated by the arrow U in FIG. 7 is, namely, 450 μm to 600 μm.

(Evaluation of the Thickness of the Diffusion Resistance Layer)

Figure 8:
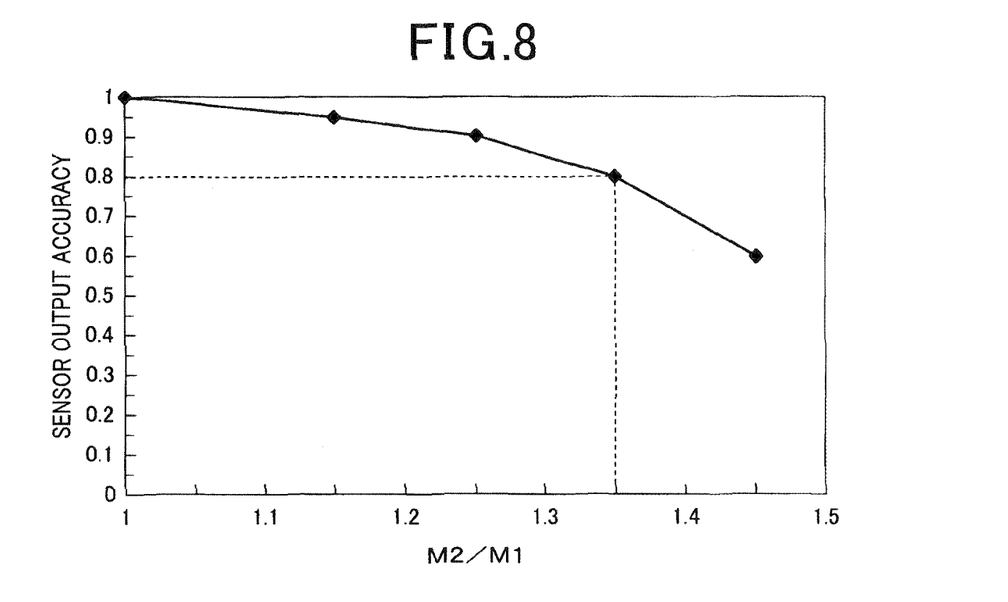
FIG. 8 is a pattern graph showing relations between the thickness of the diffusion resistance layer and the sensor output according to the first embodiment.

Relationships between the thickness M1 on the measuring electrode 13 of the diffusion resistance layer and the thickness M2 of the diffusion resistance layer on the solid electrolyte 30 other than the measuring electrode 13 and the accuracy of the sensor output were evaluated. Specifically, when the M1 and the M2 are the same, the sensor output value IL was detected and the sensor output accuracy ($IL/IL_m$) was calculated while changing a value of M2/M1. When M2/M1=1, the sensor output value $IL_m$ was set to be 1. As shown in FIG. 8, it is necessary that the sensor output accuracy ($IL/IL_m$) is not less than 0.8 to obtain the sufficient A/F detection accuracy. In addition, it is necessary that the sensor output accuracy ($IL/IL_m$) is not less than 0.9 to obtain the high further A/F detection accuracy. As shown in FIG. 8, when M2/M1≤1.35, it was shown that the sensor output accuracy ($IL/IL_m$) is not less than 0.8. Further, when M2/M1≤1.25, it was shown that the sensor output accuracy ($IL/IL_m$) is not less than 0.9.

As a result, it was confirmed that M2/M1≤1.35 is required and M2/M1≤1.25 is preferable in the thickness M1 on the measuring electrode 13 of the diffusion resistance layer 30 and the thickness M2 on the solid electrolyte 11 other than the measuring electrode 13.

(Evaluation of the Porosity of the Diffusion Resistance Layer)

Figure 9:
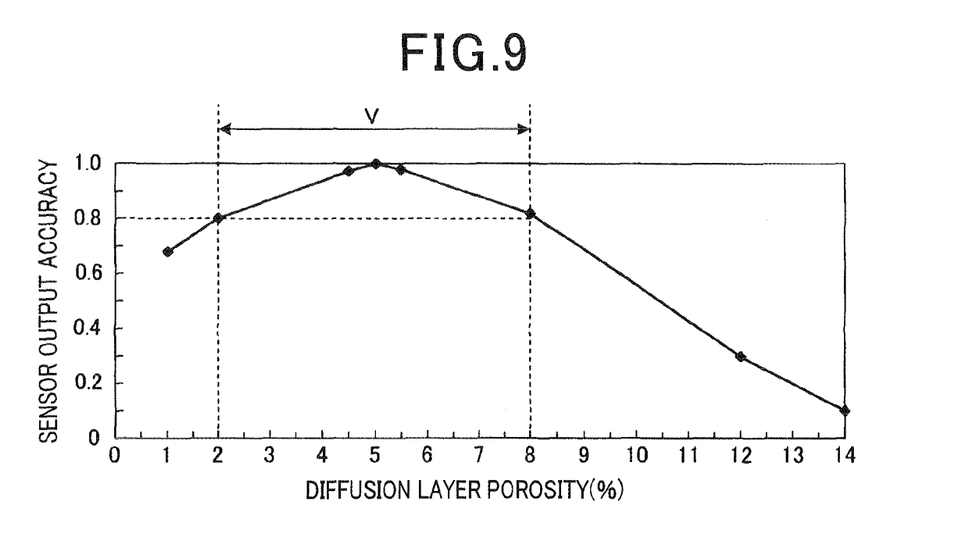
FIG. 9 shows a porosity of the diffusion resistance layer and the sensor output according to the first embodiment.

Next, the porosity of the diffusion resistance layer 30 and the sensor output accuracy were evaluated. The sensor output value IL was detected while changing the porosity of the diffusion resistance layer 30 within a range of 1.0% to 14.0%. The sensor output accuracy ($IL/IL_0$) was calculated with the sensor output $IL_0$ of an $O_2$ sensor as a standard. The $O_2$ sensor has the protection layer of 5.0% porosity which is a conventional product. It is necessary that the sensor output accuracy is not less than 0.8 to obtain sufficient A/F detection accuracy. As shown in FIG. 9, when the porosity of the diffusion resistance layer 30 is 2.0% to 8.0%, it was shown that the sensor output accuracy is not less than 0.8. Thereby, it was confirmed that the required porosity of the diffusion resistance layer 30 is 2.0% to 8.0%.

Next, functional effects in the gas sensor of the example are described below.

In the gas sensor element 10 of the example, rapid heating property of the solid electrolyte 11 is accelerated by having better heat conduction from the heater 20 to the solid electrolyte 11. This is because the heater 20 is contacted with the inside surface 11a of the solid electrolyte 11. Further, the measuring electrode 13 is provided so as to fall within a range of 0.5 mm to 7.5 mm from the tip end 11c of the solid electrolyte 11 while the length L1 in the axial direction X is 0.5 mm to 3.0 mm. That is to say, the measuring electrode 13 is formed so as to shorten sufficiently the length L1 in the axial direction X, and the measuring electrode 13 is provided so as to fall within the predetermined range from the tip end 11c of the solid electrolyte 11. Thereby, the variation of the temperature in the measuring electrode 13 and a variation of a detection performance in the measuring electrode 13 may be suppressed. Especially, a variation of a gaseous adsorption reactivity under a small amount of a gas in a stoichiometric environment is reduced, and a variation of stoichiometric detection performance is controlled. From these results, A/F just after starting the internal combustion engine and A/F with the small amount of the gas in the stoichiometric environment (ppm order) may be detected with high accuracy. In addition, mounting the gas sensor downstream of the catalyst of vehicles (rear mounting) with the small amount of the gas allows detection of A/F always with high accuracy and to be applicable to stoichiometric control.

In addition, since the diffusion resistance layer 30 is a porous material and is formed on the measuring electrode 13, a gas reaction amount in the measuring electrode 13 may be controlled.

In addition, in the gas sensor 1 of the example, the thickness M1 on the measuring electrode of the diffusion resistance layer 30 is set to be 400 µm to 700 µm. Thereby, an improvement of the A/F detection accuracy and a reduction of the consumed power and a shortening an activated time of the solid electrolyte 11 may be made compatible. Further, the thickness M1 on the measuring electrode 13 of the diffusion resistance layer 30 is set to be 450 µm to 700 µm. Thereby, the improvement of the A/F detection accuracy and the reduction of the consumed power and the shortening an activated time may be further effectively made compatible.

In addition, in the example, the porosity of the diffusion resistance layer 30 is set to be 2.0% to 8.0%. Thereby, an influence (i.e. temperature property) of a temperature variation on the A/F detection accuracy may be reduced. As a result, the A/F detection accuracy may be raised. Further, by the porosity of the diffusion resistance layer 30 being set to be 4.5% to 5.5%, the temperature property may be further reduced and the A/F detection accuracy may be further raised.

In addition, in the example, the diffusion resistance layer 30 is formed so as to be across the outside surface 13b of the measuring electrode 13 and the outside surface 11b of the solid electrolyte 11. Further, the thickness M1 on the measuring electrode 13 of the diffusion resistance layer 30 and the thickness M2 on the solid electrolyte 30 satisfy a relation of M2/M1≤1.35. Thereby, the A/F detection accuracy may be improved, and a reduction of heat stress in the sensor element 11 may be reduced. Furthermore, in the example, the improvement of the A/F detection accuracy and the reduction of heat stress may be further made compatible by being set to be M2/M1≤1.25.

In addition, in the example, the protection layer 40 is formed on the outside surface 30a of the diffusion resistance layer 30. The protection layer 40 is made up of the porous material whose porosity is higher than the porosity of the diffusion resistance layer 30. Thereby, degradation of sensor properties by poisonous substances may be prevented. Consequently, the A/F detection accuracy may be raised.

In addition, in the example, the protection layer 40 includes platinum. Thereby, the platinum used as catalyst allows promotion of burning of hydrogen gas. The hydrogen gas reaching the measuring electrode 13 may be suppressed. As a result, the hydrogen gas reach the measuring electrode 13 prior to other components in the exhaust gases, and a shift from the sensor output toward a rich side may be suppressed. As a result, the A/F detection accuracy may be raised.

In the example, the measuring electrode 13 is housed in the range (the range shown by arrow L1 in FIG. 2) which is opposed to the heating part 23 in the outside surface 11b of the solid electrolyte 11. Thereby, a heat of the heater 20 is transferred from the tip corner part 22a to the measuring electrode 13 via the solid electrolyte 11, and the heat of the heater 20 is easily reached the measuring electrode 13 by radiation. Therefore, the heat of the heater 20 easily reaches the entire measuring electrode 13 evenly. Thereby, the temperature variation of the measuring electrode 13 may be further reduced. As a result, the A/F detection accuracy may be raised.

In the example, the tip corner part 22a which is contacted with the inside surface 11a of the solid electrolyte 11 is disposed in a range of 1.5 mm to 2.0 mm from the tip end 11c of the solid electrolyte 11 in the axial direction X. Thereby, the heat of the heater 20 is easily transferred from the tip corner part 22a to the measuring electrode 13 via the solid electrolyte 11. Therefore, the temperature variation of the measuring electrode 13 may be reduced. As a result, the A/F detection accuracy may be raised.

In addition, in the example, the length L1 of the heating part 23 of the heater 20 is 3.0 mm to 7.0 mm. The heating part 23 is housed in a range of 0.25 mm to 9.0 mm from the tip end 22a of the heater 20 in the axial direction X. Thereby, the heating part 23 is disposed near side of the tip end 22a, and at least a part of the heating part 23 (full in the example) is opposed to the measuring part 13. The tip end 22a is a contact location between the solid electrolyte 11 and the heater 20. Therefore, a heat which occurs from the heating part 23 may be efficiently propagated to the measuring electrode 13 via the tip end 22a of the heater 20. Thereby, the temperature variation of the measuring electrode 13 may be further reduced. As a result, the A/F detection accuracy may be further raised.

Hereby, the example may provide the gas sensor element 10 which has the excellent rapid heating property, and capable of detecting A/F with high accuracy.

Second Embodiment

Figure 10:
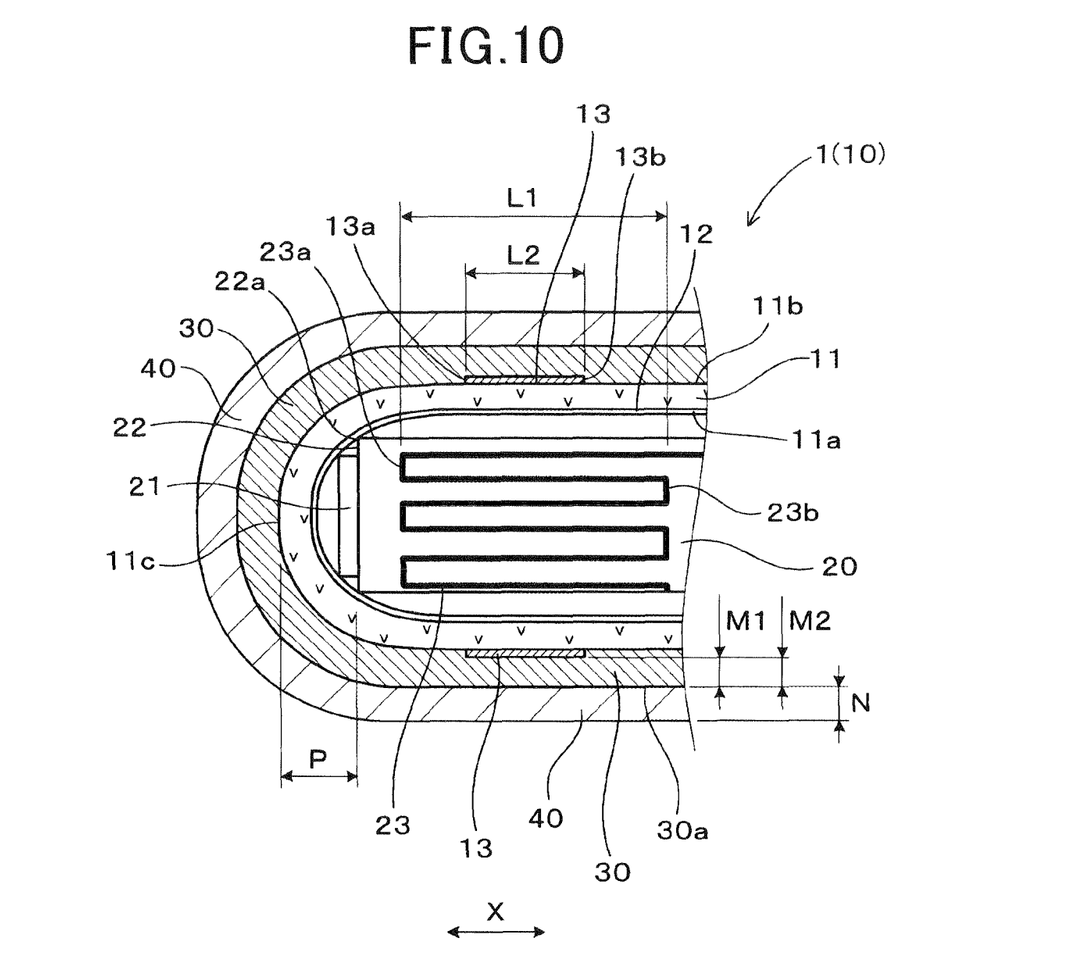
FIG. 10 shows a sectional partial enlarged view of a gas sensor element according to a second embodiment of the present invention.

In a gas sensor 1 in an example, as shown in FIG. 10, a convex part 31 of the first embodiment (refer to FIG. 2) is not formed, and a diffusion resistance layer 30 is formed so as to be M2/M1=1. That is to say, in an outside surface 30b of the diffusion resistance layer 30 and an outside surface of a protection layer 40, a part which is opposed to a measuring electrode 13 is flush with the other part respectively. Incidentally, the same reference numerals denote components equivalent to the components of the first embodiment, and the details are omitted.

The example has a functional effect equivalent to the first embodiment and also satisfies M2/M1≤1.35.

REFERENCE SIGNS LIST

1: gas sensor
10: gas sensor element
11: solid electrolyte
12: reference electrode
13: measuring electrode
20: heater
22: heating member
23: heating part 30: diffusion resistance layer
40: protection layer

What is claimed is:

1. A gas sensor element comprising:
a solid electrolyte which has a cup-shaped closed-end cylindrical shape;
a reference electrode which is formed on an inside surface of the solid electrolyte;
a measuring electrode which is formed on an outside surface of the solid electrolyte; and
a heater which has a heating part heating the solid electrolyte and a tip end is disposed inside the solid electrolyte so as to contact the inside surface of the solid electrolyte,
wherein the gas sensor element is a limiting current type gas sensor element configured to output a limiting current value depending on specific concentration of measured gases by applying predetermined voltage between the reference electrode and the measuring electrode,
wherein a length of the measuring electrode in an axial direction is 0.5 mm to 3.0 mm, and the measuring electrode being provided so as to fall within a range of 0.5 mm to 7.5 mm from a tip end of the solid electrolyte in the axial direction.

2. The gas sensor element as set forth in claim 1, wherein a diffusion resistance layer, which is made up of a porous body covering at least the measuring electrode, is disposed outside the solid electrolyte.

3. The gas sensor element as set forth in claim 2, wherein a thickness on the measuring electrode of the diffusion resistance layer is 400 μm to 700 μm.

4. The gas sensor element as set forth in claim 2, wherein the thickness on the measuring electrode of the diffusion resistance layer is 450 μm to 600 μm.

5. The gas sensor element as set forth in claim 2, wherein a porosity of the diffusion resistance layer is 2.0% to 8.0%.

6. The gas sensor element as set forth in claim 2, wherein a porosity of the diffusion resistance layer is 4.5% to 5.5%.

7. The gas sensor element as set forth in claim 2, wherein the diffusion resistance layer is formed so as to be across an outside surface of the measuring electrode and the outside surface, the thickness of a portion of the diffusion resistance layer located above the measuring electrode being defined as M1 and a thickness of a portion of the diffusion resistance layer located above the outside surface of the solid electrolyte being defined as M2, a value of M2/M1 being not more than 1.35.

8. The gas sensor element as set forth in claim 2, wherein the diffusion resistance layer is formed so as to be across an outside surface of the measuring electrode and the outside surface, the thickness of a portion of the diffusion resistance layer located above the measuring electrode being defined as M1 and a thickness of a portion of the diffusion resistance layer located above the outside surface of the solid electrolyte being defined as M2, a value of M2/M1 being not more than 1.25.

9. The gas sensor element as set forth in claim 2, further comprising a protection layer formed on an outside surface of the diffusion resistance layer, wherein the protection layer is made of a porous material having a porosity higher than the porosity of the diffusion resistance layer.

10. The gas sensor element as set forth in claim 9, wherein at least a part of the protection layer includes platinum.

11. The gas sensor element as set forth in claim 1, wherein the measuring electrode is located to face a part of the outside surface of the solid electrolyte, the part of the outside surface facing the heating part.

12. The gas sensor element as set forth in claim 1, wherein the tip end, which contacts the inside surface of the solid electrolyte in the heater, is located within a range of 1.5 mm to 2.0 mm from the tip end of the solid electrolyte in the axial direction.

13. The gas sensor element as set forth in claim 1, wherein a length of the heating part in the axial direction is 3.0 mm to 7.0 mm, the heating part in the axial direction being housed in a range of 0.25 mm to 9.0 mm from the tip end of the heater.

* * * * *